(12) United States Patent
Garlow (10) Patent No.: US 10,238,353 B2
(45) Date of Patent: *Mar. 26, 2019

(54) APPARATUS AND METHOD OF COUNTERBALANCING AXES AND MAINTAINING A USER SELECTED POSITION OF A X-RAY SCANNER GANTRY

(71) Applicant: Medtronic Navigation, Inc., Louisville, CO (US)

(72) Inventor: David A. Garlow, Lynnfield, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 23 days.

This patent is subject to a terminal disclaimer.

(21) Appl. No.: 15/886,473

(22) Filed: Feb. 1, 2018

(65) Prior Publication Data

US 2018/0153491 A1 Jun. 7, 2018

Related U.S. Application Data

(63) Continuation of application No. 14/663,020, filed on Mar. 19, 2015, now Pat. No. 9,883,843.

(51) Int. Cl.
*A61B 6/00* (2006.01)
(52) U.S. Cl.
CPC .......... *A61B 6/4476* (2013.01); *A61B 6/4405* (2013.01); *A61B 6/4435* (2013.01); *A61B 6/4482* (2013.01)
(58) Field of Classification Search
CPC .... A61B 6/4405; A61B 6/4476; A61B 6/4482
See application file for complete search history.

(56) References Cited

U.S. PATENT DOCUMENTS 4,163,929 A 8/1979 Janu et al.
6,940,941 B2 9/2005 Gregerson et al.
(Continued)

FOREIGN PATENT DOCUMENTS

EP 2201894 A1 6/2010
EP 2427110 A1 3/2012
WO 2010128417 A1 11/2010

OTHER PUBLICATIONS

International Preliminary Report on Patentability dated Sep. 28, 2017 in corresponding International Application No. PCT/US2016/021292.
(Continued)

*Primary Examiner* — Chih-Cheng Kao
(74) *Attorney, Agent, or Firm* — Harness, Dickey & Pierce, P.L.C.

(57) ABSTRACT

A system including an input sensor, a summer, a controller, and a feedback sensor. The input sensor: detects a first amount of force or torque applied on a component of an x-ray scanner gantry in a direction; and generates a command signal. The command signal indicates the first amount of force or torque. The summer generates an error signal based on the command signal and a feedback signal. The controller controls operation of a motor based on the error signal to: reduce the error signal; provide counterbalancing of the gantry in the direction; and provide a net force or torque on the gantry that is equal to a predetermined value or is within a predetermined range of the predetermined value. The feedback sensor detects a second amount of force or torque applied on the gantry in the direction as a result of the controlled operation and generates the feedback signal.

20 Claims, 5 Drawing Sheets

(56) References Cited

U.S. PATENT DOCUMENTS

| | | |
|---|---|---|
| 7,001,045 B2 | 2/2006 | Gregerson et al. |
| 7,188,998 B2 | 3/2007 | Gregerson et al. |
| 7,338,207 B2 | 3/2008 | Gregerson et al. |
| 7,490,982 B2 | 2/2009 | Gregerson et al. |
| 7,905,659 B2 | 3/2011 | Gregerson et al. |
| 8,308,361 B2 | 11/2012 | Gregerson et al. |
| 8,746,973 B2 | 6/2014 | Gregerson et al. |
| 9,883,843 B2 * | 2/2018 | Garlow .............. A61B 6/4476 |
| 2008/0123811 A1 | 5/2008 | Curtis |
| 2012/0106701 A1 | 5/2012 | Meek et al. |
| 2014/0328456 A1 | 11/2014 | Lee et al. |
| 2015/0313561 A1 | 11/2015 | Kwak |

OTHER PUBLICATIONS

International Search Report and Written Opinion dated Jun. 27, 2016 for PCT/US2016/021292 claiming benefit of U.S. Appl. No. 14/663,020, filed Mar. 19, 2016.

* cited by examiner

APPARATUS AND METHOD OF COUNTERBALANCING AXES AND MAINTAINING A USER SELECTED POSITION OF A X-RAY SCANNER GANTRY

CROSS-REFERENCE TO RELATED APPLICATIONS

This application is a continuation of U.S. patent application Ser. No. 14/663,020 filed on Mar. 19, 2015. The entire disclosure of the above application is incorporated herein by reference.

FIELD

The present disclosure relates to x-ray imaging systems, and more particularly to positioning an x-ray scanner gantry.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the patient based on images of the patient, which can be acquired using an x-ray scanner having an imaging system. The images may be acquired prior to or during the procedure. The imaging system may be, for example, an O-Arm or C-arm imaging system. The images may be fluoroscopic or radiographic images depending on an operating mode of the imaging system.

The acquired images of the patient can assist a surgeon in planning and performing the procedure. A surgeon may select a two dimensional image or a three dimensional image representation of the patient. The images can assist the surgeon in performing a procedure with a less invasive technique by allowing the surgeon to view the anatomy of the patient without removing overlying tissue (including dermal and muscular tissue) when performing a procedure.

An O-Arm imaging system includes an 'O'-shaped gantry and a 'O'-shaped rotor. A C-Arm imaging system includes a 'C'-shaped gantry and a 'C'-shaped rotor. Each of these imaging systems typically includes an x-ray source and a x-ray detector mounted opposite each other on the corresponding rotor. Each of the x-ray sources generates x-rays, which are directed at a subject. Each of the x-ray detectors detects the x-rays subsequent to the x-rays passing through the subject.

An O-Arm (or C-Arm) gantry may have multiple axes (e.g., a x-axis, a y-axis, a z-axis, a wag axis, and a tilt axis) over which the gantry may be moved into position for surgery. The gantry is heavy and may be positioned for surgery by using a pendant (or remote control device) and manually jogging each of the axes one at a time until the gantry is in a selected position for surgery. This is typically a two person activity where a first person is on a near side of the gantry and is driving each of the axes while the other person is watching a far side of the gantry to indicate to the first person any potential interferences with a surgical table, a patient, or other devices and/or items in an area of the gantry.

SUMMARY

This section provides a general summary of the disclosure, and is not a comprehensive disclosure of its full scope or all of its features.

According to various embodiments, provided is a system that includes an input sensor, a summer, a controller, and a feedback sensor. The input sensor is configured to (i) detect a first amount of force or torque applied by a user on a component of an x-ray scanner gantry in a direction, and (ii) generate an input command signal. The input command signal indicates the first amount of force or torque. The summer is configured to generate an error signal based on the input command signal and a feedback signal. The controller is configured to control operation of a motor based on the error signal to (i) reduce the error signal, (ii) provide counterbalancing of the x-ray scanner gantry in the direction, and (iii) provide a net force or torque on the x-ray scanner gantry in the direction that is equal to a predetermined value or is within a predetermined range of the predetermined value. The feedback sensor is configured to (i) detect a second amount of force or torque applied on the x-ray scanner gantry in the direction as a result of the controlled operation of the motor, and (ii) generate the feedback signal based on the amount of force or torque.

In other features, a system is provided and includes an input sensor, a summer, a controller, and a feedback sensor. The input sensor is configured to (i) detect movement of a component of an x-ray scanner gantry by a user, and (ii) generate an input command signal, wherein the input command signal commands movement of the x-ray scanner gantry in a direction. The summer is configured to generate an error signal based on the input command signal and a feedback signal. The controller is configured to control operation of a motor based on the error signal to (i) reduce the error signal, (ii) provide counterbalancing of the x-ray scanner gantry in the direction, and (iii) provide a net force on the x-ray scanner gantry in the direction that is equal to a predetermined value or is within a predetermined range of the predetermined value. The feedback sensor is configured to (i) detect movement of the x-ray scanner gantry in the direction as a result of the controlled operation of the motor, and (ii) generate the feedback signal based on the detected movement.

In other features, a method is provided and includes: detecting, via an input sensor, a first amount of force or torque applied by a user on a component of an x-ray scanner gantry in a direction; and generating an input command signal, where the input command signal indicates the first amount of force or torque. The method further includes: generating an error signal based on the input command signal and a feedback signal; and controlling operation of a motor based on the error signal to (i) reduce the error signal, (ii) provide counterbalancing of the x-ray scanner gantry in the direction, and (iii) provide a net force or torque on the x-ray scanner gantry in the direction that is equal to a predetermined value or is within a predetermined range of the predetermined value. The method yet further includes: detecting, via a feedback sensor, a second amount of force or torque applied on the x-ray scanner gantry in the first direction as a result of the controlled operation of the motor; and generating the feedback signal based on the second amount of force or torque.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

To overcome the disadvantages associated with traditional positioning techniques of a gantry, examples of gantry positioning systems are disclosed herein. The gantry positioning systems include zero-force systems, which allow a user (or surgeon) to physically move a gantry, via a component (e.g., a handle) or other input control device (e.g., a joystick), into position with minimal force physically applied by the user. As an analogical example, a dentist may move a light over a patient in order to view inside a mouth of the patient. The dentist may grab an end of the light and manually manipulate the light to a selected position. Once the light is in the selected position, the dentist lets go of the light and the light remains in the selected position. The gantry positioning systems disclosed herein allow a user to manually move a gantry to a selected position and let go of the component or the input control device and the gantry remains in the selected position.

The following description is merely exemplary in nature. It should be understood that throughout the drawings, corresponding reference numerals indicate like or corresponding parts and features. As indicated above, the present teachings are directed toward an imaging system, such as an O-Arm or C-Arm imaging system. It should be noted, however, that the teachings disclosed herein are applicable to other imaging systems.

Figure 1:
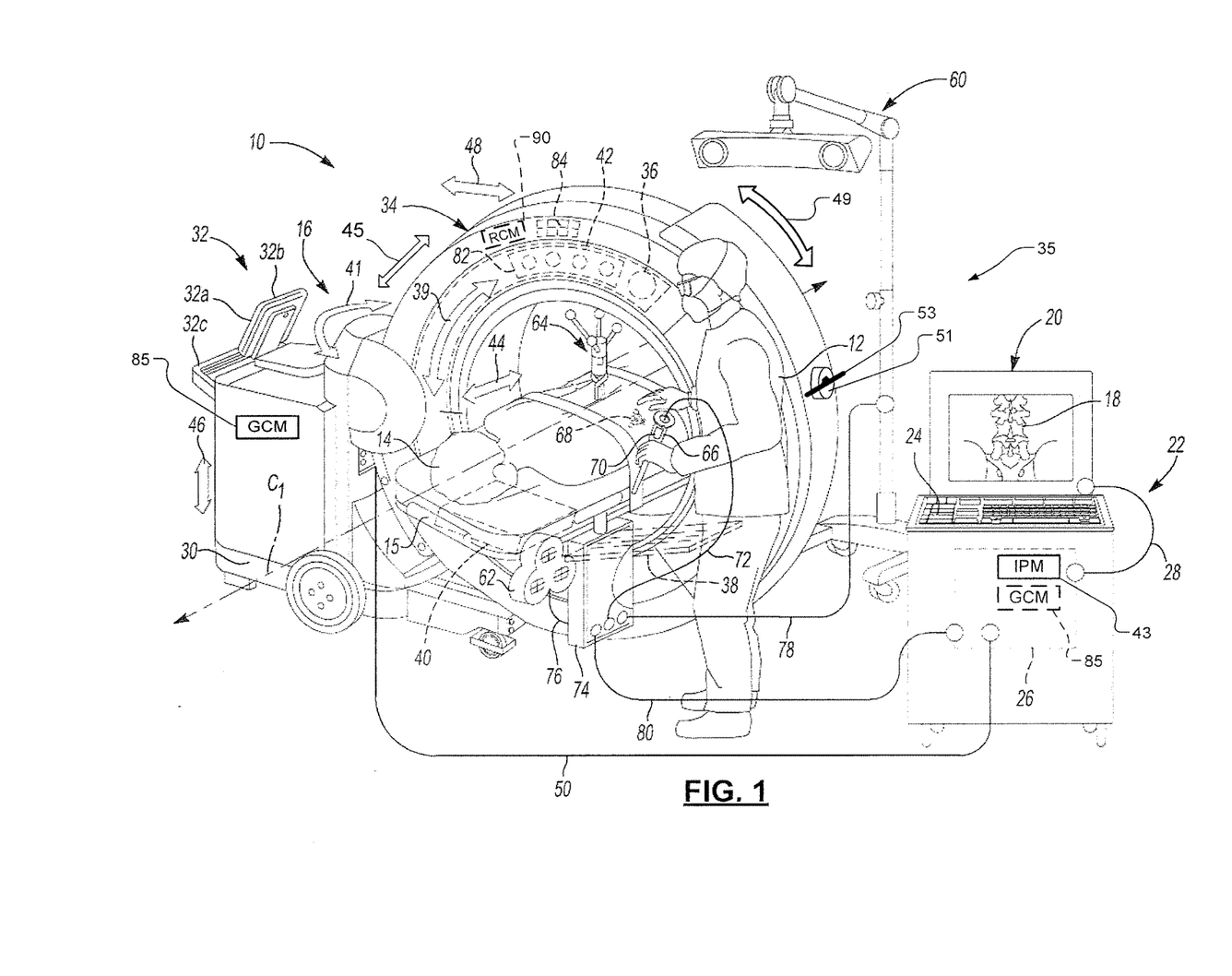
FIG. 1 is an environmental view of an imaging system in an operating theatre, including gantry positioning system in accordance with an embodiment of the present disclosure.

FIG. 1 shows an operating theatre (or inside of an operating room) 10 and a user 12 (e.g., a physician) performing a procedure on a subject (e.g., a patient) 14. In performing the procedure, the user 12 uses an imaging system 16 to acquire image data of the patient 14. The image data acquired of the patient 14 can include two-dimension (2D) or three-dimensional (3D) images. Models may be generated using the acquired image data. The model can be a three-dimension (3D) volumetric model generated based on the acquired image data using various techniques, including algebraic iterative techniques. The image data (designated 18) can be displayed on a display device 20, and additionally, may be displayed on a display device 32a associated with an imaging computing system 32. The displayed image data 18 may include 2D images, 3D images, and/or a time changing 4D images. The displayed image data 18 may also include acquired image data, generated image data, and/or a combination of the acquired and generated image data.

Image data acquired of a patient 14 may be acquired as 2D projections. The 2D projections may then be used to reconstruct 3D volumetric image data of the patient 14. Also, theoretical or forward 2D projections may be generated from the 3D volumetric image data. Accordingly, image data may be used to provide 2D projections and/or 3D volumetric models.

The display device 20 may be part of a computing system 22. The computing system 22 may include a variety of computer-readable media. The computer-readable media may be any available media that is accessed by the computing system 22 and may include both volatile and non-volatile media, and removable and non-removable media. By way of example, the computer-readable media may include computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors may include multiple-processing core processors, microprocessors, etc.) that may be incorporated with the computing system 22. The input device 24 may include any suitable device to enable a user to interface with the computing system 22, such as a touchpad, touch pen, touch screen, keyboard, mouse, joystick (sometimes referred to as a joystick controller), trackball, wireless mouse, audible control or a combination thereof. Furthermore, while the computing system 22 is described and illustrated herein as comprising the input device 24 discrete from the display device 20, the computing system 22 may include a touchpad or tablet computing device and may be integrated within or be part of the imaging computing system 32. A connection (or communication line) 28 may be provided between the computing system 22 and the display device 20 for data communication to allow driving the display device 20 to illustrate the image data 18.

The imaging system 16 may be an O-Arm imaging system, a C-Arm imaging system or other suitable imaging system. The imaging system 16 may include a mobile cart 30, the imaging computing system 32 and a gantry 34 (or x-ray scanner gantry). The gantry 34 includes an x-ray source 36, a collimator (not shown), a multi-row detector 38, a flat panel detector 40 and a rotor 42. The mobile cart 30 may be moved from one operating theater or room to another and the gantry 34 may be moved relative to the mobile cart 30. This allows the imaging system 16 to be mobile and used for various procedures without requiring a capital expenditure or space dedicated to a fixed imaging system. Although the gantry 34 is shown as being mobile, the gantry 34 may not be connected to the mobile cart 30.

The imaging system 16, the mobile cart 30 and/or the imaging computing system 32 may include motors, positioning devices, coupling members, circuit elements, controllers (or control modules), sensors, etc. (examples of which are shown in and described with respect to FIGS. 2-5) for moving and orienting the gantry 34 relative to the table 15 and/or the patient 14. The motors, positioning devices, coupling members, circuit elements, controllers (or control modules), sensors, etc. are part of a gantry positioning system 35. The gantry positioning system 35 is configured to allow a user to manually move and orient the gantry 34 into a selected position with minimal effort. Examples of portions of the gantry positioning system 35 are shown and described with respect to FIGS. 2-5.

The gantry 34 may define an isocenter of the imaging system 16. In this regard, a centerline C1 through the gantry 34 defines an isocenter or center of the imaging system 16. Generally, the patient 14 can be positioned along the centerline C1 of the gantry 34, such that a longitudinal axis of the patient 14 is aligned with the isocenter of the imaging system 16.

The imaging computing system 32 may control the movement, positioning and adjustment of the multi-row detector 38, the flat panel detector 40 and the rotor 42 independently to enable image data acquisition via an image processing module 43 of the processor 26. The processed images may be displayed on the display device 20.

During operation, the source 36 emits x-rays through the patient 14, which are detected by the multi-row detector 38 or the flat panel detector 40. The x-rays emitted by the source 36 may be shaped by the collimator and emitted for detection by the multi-row detector 38 or the flat panel detector 40. The collimator may include one or more leaves, which may be controlled to shape the x-rays emitted by the source 36. The collimator may shape the x-rays emitted by the source 36 into a beam that corresponds with the shape of the multi-row detector 38 and the flat panel detector 40. The multi-row detector 38 may be selected to acquire image data of low contrast regions of the anatomy, such as regions of soft tissue. The flat panel detector 40 may be selected to acquire image data of high contrast regions of the anatomy, such as bone. The source 36, the collimator, the multi-row detector 38 and the flat panel detector 40 may each be coupled to and/or mounted on the rotor 42.

The multi-row detector 38 and the flat panel detector 40 may be coupled to the rotor 42 to be (i) diametrically opposed from the source 36 and the collimator within the gantry 34, and (ii) independently movable relative to each other and into alignment with the source 36 and the collimator. In one example, the multi-row detector 38 may be positioned such that the flat panel detector 40 may be adjacent to the multi-row detector 38. In one alternative example, the flat panel detector 40 may be moved over the multi-row detector 38 into alignment with the source 36 when an image using the flat panel detector 40 is acquired. In another example, the multi-row detector 38 may be positioned over the flat panel detector 40. As a further alternative, the multi-row detector 38 and the flat panel detector 40 may each be separately movable, such that the selected multi-row detector 38 or flat panel detector 40 may be aligned with the source 36 and the collimator. The selected one of the multi-row detector 38 and the flat panel detector 40 may be aligned with the source 36 and the collimator when the selected one of the multi-row detector 38 and the flat panel detector 40 is substantially opposite or about 180 degrees apart from the source 36 and the collimator.

As the source 36, collimator, multi-row detector 38 and flat panel detector 40 are coupled to the rotor 42, the source 36, collimator, multi-row detector 38 and flat panel detector 40 are movable within the gantry 34 about the patient 14. Thus, the multi-row detector 38 and the flat panel detector 40 are able to be rotated in a 360° motion around the patient 14, as indicated by arrow 39. The source 36 and collimator may move in concert with at least one of the multi-row detector 38 and the flat panel detector 40 such that the source 36 and collimator remain generally 180° apart from and opposed to the multi-row detector 38 or flat panel detector 40.

The gantry 34 has multiple degrees of freedom of motion. The gantry 34 may be isometrically swayed or swung (herein also referred to as iso-sway) relative to table 15 on which the patient 14 is disposed. The isometric swing (sometimes referred to as a wag (or yaw) angle or wag axis) is indicated by arrow 41. The gantry 34 may be: tilted relative to the patient 14 as indicated by arrow 45 (sometimes referred to as the tilt (or roll) angle or tilt axis); moved longitudinally relative to the patient 14 as indicated by arrow 44 (sometimes referred to as the z-axis); moved up and down relative to the mobile cart 30 and transversely to the patient 14 as indicated by arrow 46 (sometimes referred to as the y-axis); moved away from or towards the mobile cart 30 as indicated by arrow 48 (sometimes referred to as the x-axis); and rotated about a point on the mobile cart 30 as indicated by arrow 49 (sometimes referred to as a pitch angle or pitch axis). The degrees of freedom of motion may be represented using the Cartesian coordinate system. These degrees of freedom of motion are provided by the gantry positioning system 35 and allow a user to move the gantry relative to the table 15 and the patient 14 with minimal effort by the user. These different degrees of freedom of motion of the gantry 34 allow the source 36, collimator, multi-row detector 38 and flat panel detector 40 to be positioned relative to the patient 14.

The gantry positioning system 35, as shown in the example of FIG. 1, may include an input sensor 51 and a component (or handle) 53. The input sensor 51 may be a six degree of freedom (DOF) sensor. The input sensor 51 may be used to detect position, velocity, acceleration, force, and/or torque based on movement of and/or force applied on the handle 53. The input sensor 51 may be mounted on the gantry 34 as shown or may located elsewhere on or in the gantry 34, the imaging computing system 32, the mobile cart 30, the computing system 22, etc. The handle 53 may be connected to the sensor 51 as shown or may be part of a joystick. The joystick may include encoders or other optical sensors to detect motion of the joystick. The input sensor 51 may be hard mounted to the gantry 34 or may be located elsewhere. By mounting the sensor 51 and the handle 53 on an end of the gantry 34 (in the x-axis direction) as shown, the user is able to see both near and far sides of the gantry in the z-direction when standing by the handle 53.

The input sensor 51 may include a collection of sensors. The input sensor 51 may include: a combination of linear and/or rotary encoders assembled into a six DOF sensing module; a set of optical sensors assembled into a six DOF sensing module; a set of load cells and/or strain gauges assembled into a six DOF sensing module; and/or a set of accelerometers and/or gyroscopes assembled into a six DOF sensing module. The input sensor 51 may include any number of encoders (linear and/or rotary encoders), optical sensors, load cells, strain gauges, accelerometers, gyroscopes, and/or other sensors. The input sensor 51 may include a six degree of freedom load cell (or force/torque sensor). The input sensor 51 may include a multi-axis gimbal to provide six degrees of freedom of movement of the handle 53. The six degrees of freedom of motion of the handle 53 may be translated into corresponding motion of the gantry 34. The input sensor 51 may be an inertial measurement device (sometimes referred to as an inertial measurement unit (IMU)) and include 3 accelerometers and 3 gyroscopes. If the sensor 51 includes encoders or optical sensors, the encoders and optical sensors may be used to detect position, velocity and/or acceleration depending on the types of encoders and optical sensors and the corresponding signal processing circuitry used. If the sensor 51 includes and/or is implemented as an IMU, the sensor 51 may be used to measure velocity and/or acceleration. The load cells and strain gauges may be used to detect force and/or torque.

The imaging system 16 may be precisely controlled by the imaging computing system 32 to move the source 36, collimator, the multi-row detector 38 and the flat panel detector 40 relative to the patient 14 to generate precise image data of the patient 14. In addition, the imaging system 16 may be connected with the processor 26 via connection 50 which includes a wired or wireless connection or physical media transfer from the imaging system 16 to the processor 26. Thus, image data collected with the imaging system 16 may also be transferred from the imaging computing system 32 to the computing system 22 for navigation, display, reconstruction, etc.

The imaging system 16 may also be used during an unnavigated or navigated procedure. In a navigated procedure, a localizer, including either or both of an optical localizer 60 and an electromagnetic localizer 62, may be used to generate a field or receive or send a signal within a navigation domain relative to the patient 14. If desired, the components of a navigation system associated with performing a navigated procedure may be integrated within the imaging system 16. The navigated space or navigational domain relative to the patient 14 may be registered to the image data 18 to allow registration of a navigation space defined within the navigational domain and an image space defined by the image data 18. A patient tracker (or a dynamic reference frame) 64 may be connected to the patient 14 to allow for a dynamic registration and maintenance of the registration of the patient 14 to the image data 18.

An instrument 66 may then be tracked relative to the patient 14 to allow for a navigated procedure. The instrument 66 may include an optical tracking device 68 and/or an electromagnetic tracking device 70 to allow for tracking of the instrument 66 with either or both of the optical localizer 60 or the electromagnetic localizer 62. The instrument 66 may include a communication line 72 with a navigation interface device 74, which may communicate with the electromagnetic localizer 62 and/or the optical localizer 60. The navigation interface device 74 may then communicate with the processor 26 via a communication line 80. The connections or communication lines 28, 50, 76, 78, or 80 can be wire based as shown or the corresponding devices may communicate wirelessly with each other. The imaging system 16 having the integrated navigation system tracks the instrument 66 relative to the patient 14 to allow for illustration of the tracked location of the instrument 66 relative to the image data 18 for performing a procedure.

The instrument 66 may be an interventional instrument and/or an implant. Implants may include a ventricular or vascular stent, a spinal implant, neurological stent or the like. The instrument 66 may be an interventional instrument such as a deep brain or neurological stimulator, an ablation device, or other appropriate instrument. Tracking the instrument 66 allows for viewing the location of the instrument 66 relative to the patient 14 with use of the registered image data 18 and without direct viewing of the instrument 66 within the patient 14. For example, the instrument 66 may be graphically illustrated as an icon superimposed on the image data 18.

Further, the imaging system 16 may include a tracking device, such as an optical tracking device 82 or an electromagnetic tracking device 84 to be tracked with a respective optical localizer 60 or the electromagnetic localizer 62. The tracking devices 82, 84 may be associated directly with the source 36, multi-row detector 38, flat panel detector 40, rotor 42, the gantry 34, or other appropriate part of the imaging system 16 to determine the location or position of the source 36, multi-row detector 38, flat panel detector 40, rotor 42 and/or gantry 34 relative to a selected reference frame. As illustrated, the tracking devices 82, 84 may be positioned on the exterior of the housing of the gantry 34. Accordingly, portions of the imaging system 16 including the instrument 66 may be tracked relative to the patient 14 to allow for initial registration, automatic registration or continued registration of the patient 14 relative to the image data 18.

The image processing module 43 may receive user input data from the input device 32c and may output the image data 18 to the display device 20 or the display device 32a. The user input data may include a request to acquire image data of the patient 14. Based on the user input data, the image processing module 43 may generate a detector signal and a motion signal. The detector signal may include a selected detector for image acquisition. The motion signal may include a motion profile for the rotor 42 to move to a selected location to acquire image data. The motion signal may be a command or instruction signal that is provided from the image processing module to a gantry control module 85. The gantry control module 85 may be included in the imaging computing system 32, on the mobile cart 30, or as part of the processor 26. The image processing module 43 may also send a source signal to the source 36. The source signal may command the source 36 to output or emit at least one or more x-ray pulses. The image processing module 43 may also send a collimator signal to the collimator. The collimator signal may indicate a selected shape of one or more collimated x-ray pulses. The selected shape of the collimated x-ray pulses may correspond to the selected one of the multi-row detector 38 and the flat panel detector 40. In this regard, if the multi-row detector 38 is selected, the collimated x-ray pulses may be shaped by the collimator to match the shape of the multi-row detector 38. If the flat panel detector 40 is selected, then the collimated x-ray pulses may be shaped by the collimator to match the shape of the flat panel detector 40.

The image processing module 43 may also receive as input a multi-row detector signal, which may include the one or more collimated x-ray pulses detected by the multi-row detector 38. The image processing module 43 may receive as input a flat panel detector signal, which may include the one or more collimated x-ray pulses detected by the flat panel detector 40. Based on the received collimated x-ray pulses, the image processing module 43 may generate the image data 18.

In one example, the image data 18 may include a single 2D image. In another example, the image processing module 43 may perform automatic reconstruction of an initial 3D model of an area of interest of the patient 14. Reconstruction of the 3D model may be performed in any appropriate manner, such as using algebraic techniques for optimization. The algebraic techniques may include Expectation maximization (EM), Ordered Subsets EM (OS-EM), Simultaneous Algebraic Reconstruction Technique (SART) and total variation minimization. A 3D volumetric reconstruction may be provided based on the 2D projections.

The algebraic techniques may include an iterative process to perform a reconstruction of the patient 14 for display as the image data 18. For example, a pure or theoretical image data projection, based on or generated from an atlas or stylized model of a "theoretical" patient, may be iteratively changed until the theoretical projection images match the acquired 2D projection image data of the patient 14. Then, the stylized model may be appropriately altered as the 3D volumetric reconstruction model of the acquired 2D projection image data of the patient 14 and may be used in a surgical intervention, such as navigation, diagnosis, or planning interventions. In this regard, the stylized model may provide additional detail regarding the anatomy of the patient 14, which may enable the user 12 to plan the surgical intervention efficiently. The theoretical model may be associated with theoretical image data to construct the theoretical model. In this way, the model or the image data 18 may be built based upon image data acquired of the patient 14 with the imaging system 16. The image processing module 43 may output the image data 18 to the display device 32*a*.

The gantry control module 85 may receive as an input the detector signal and the motion signal from the image processing module 43. The gantry control module 85, based on the detector signal and the motion signal may transmit (via wires or wirelessly) control signals to a rotor control module 90. The rotor control module 90 may be located on the rotor 42. Based on the detector signal, the gantry control module 85 may generate a first move signal to move the selected one of the multi-row detector 38 or the flat panel detector 40 into alignment with the source 36 and the collimator. Based on the motion signal, the gantry control module 85 may also generate a second move signal for the rotor 42 to move or rotate the rotor 42 within the gantry 34 relative to the patient 14. A third move signal may be generated based on the motion signal and provided to the rotor control module 90. The rotor 42 may be rotated to move the source 36, the collimator, the multi-row detector 38 and the flat panel detector 40 360° around the longitudinal axis of the patient 14 within the gantry 34. The rotor may be continuously rotated in a single direction more than 360°. The movement of the source 36, the collimator, the multi-row detector 38 and the flat panel detector 40 about the patient 14 may be controlled to acquire image data at selected locations and orientations relative to the patient 14.

The 2D image data may be acquired at each of multiple annular positions of the rotor 42. The 3D image data may be generated based on the 2D image data. Also, the gantry 34, the source 36, the multi-row detector 38 and the flat panel detector 40 may not be moved in a circle, but rather may be moved in another pattern, such as a spiral helix, or other rotary movement about or relative to the patient 14. This can reduce exposure of a patient to radiation. The pattern (or path) may be non-symmetrical and/or non-linear based on movements of the imaging system 16, such as the gantry 34. In other words, the path may not be continuous in that the gantry 34 may be stopped and moved back in a direction along the path the gantry 34 previously followed. This may include following previous oscillations of the gantry 34.

Inputs to the imaging system 16 may be received at the input device 32*c*, input device 24, or other control modules (not shown) within the computing system 22 or imaging computing system 32, and/or determined by other sub-modules (not shown) within the image processing module 43. The image processing module 43 may receive user input data requesting that image data of the patient 14 be acquired. The input data may include information as to whether the region of interest on the patient 14 is a high contrast region (e.g. boney tissue) or a low contrast region (e.g. soft tissue). In one example, the user input data may include a region of interest on the anatomy of the patient 14. The image processing module 43 may automatically determine to use the multi-row detector 38 or the flat panel detector 40 based on the region of interest. For example, the user may select (i) the multi-row detector 38 to acquire an image of soft tissue, and (ii) the flat panel detector 40 to acquire an image of boney tissue.

Based on the user input data, the image processing module 43 may generate source data and detector type data. The image processing module 43 may also generate motion profile data and collimator data. The source data may include information to output x-ray pulses or a signal to power-down the imaging system 16. The detector type data may include the selected multi-row detector 38 or flat panel detector 40 to acquire the image data. The motion profile data may include a selected profile for the movement of the rotor 42 within the gantry 34. The collimator data may include information to shape the x-ray pulses into collimated x-ray pulses to match the selected one of the multi-row detector 38 and flat panel detector 40.

The image processing module 43 may also receive as an input multi-row detector data and flat panel detector data. The multi-row detector data may indicate the energy from the collimated x-ray pulses received by the multi-row detector 38. The flat panel detector data may indicate the energy from the collimated x-ray pulses received by the flat panel detector 40. Based on the multi-row detector data and the flat panel detector data, the image processing module 43 may generate the image data 18 and may output this image data 18 to the display device 32*a* or display device 20.

The gantry control module 85 may receive as input the detector type data and the motion profile data. Based on the detector type data, the gantry control module 85 may generate flat panel move data or multi-row move data (and/or corresponding signals). The flat panel move data may include a selected position for the flat panel detector 40 to move to in order to be aligned with the source 36 and collimator. The multi-row move data may include a selected position for the multi-row detector 38 to move in order to be aligned with the source 36 and collimator.

The processor 26 or a module thereof, based on the source data, may cause the source 36 to generate pulse data for control of the collimator. The pulse data may include pulse data for at least one x-ray pulse. The processor 26 and/or a module thereof may receive as an input the multi-row move data and the collimated pulse data. Based on the multi-row move data, the multi-row detector 38 may move into alignment with the source 36. Based on the received pulse data, the processor 26 and/or a module thereof may generate the multi-row detector data (and/or a corresponding signal) for the image processing module 43. The processor 26 and/or a module thereof may receive as an input the flat panel move data and the collimated pulse data. Based on the flat panel move data, the flat panel detector 40 may move into alignment with the source 36. Based on the received pulse data, the flat panel control module may generate the flat panel detector data (and/or a corresponding signal) for the image processing module 43.

Based on the motion profile data, the gantry control module 85 may generate rotor move data (and/or a corresponding signal) for the rotor control module 90. The rotor move data may indicate a selected movement profile for the rotor 42 to move within the gantry 34 to enable the acquisition of the image data. The rotor control module 90 may receive as an input the rotor move data. Based on the rotor move data, the rotor 42 may be moved within the gantry 34 to a desired location in order to acquire the image data.

The sensor 51 may be connected via wires (or other point-to-point electrically conductive elements) to or wirelessly communicate with the processor 26, the gantry control module 85, the rotor control module 90, and/or other controllers and/or modules of the systems 16, 22, 32. For example, if the sensor 51 is implemented as an IMU, the sensor 51 may wirelessly communicate with the processor 26, the gantry control module 85, rotor control module 90, and/or other controllers and/or modules of the systems 16, 22, 32. The sensor 51, the processor 26, the gantry control module 85, and the rotor control module 90 may include transceivers with respective medium access control (MAC) modules and physical layer (PHY) modules for wireless communication with each other. The sensor 51, the processor 26, the gantry control module 85, and/or the rotor control module 90 may provide position control, velocity control, acceleration control, force control and/or torque control for the movement of the gantry 34. The sensors, modules, processors and/or controllers of the systems 16, 22, 32 may communicate with each other and share data, signals and/or information disclosed herein.

In order to provide the six degrees of freedom described above and allow the user to manually, physically, and effortlessly move the gantry 34 into place, a zero-force control system may be provided for each degree of freedom. Each zero-force control system has one or more input sensors, controllers (or control modules), amplifiers, motors, coupling members, feedback sensors, etc. The zero-force control systems may share input sensors, controllers, coupling members, feedback sensors, etc. Note that if the sensor 51 and the handle 53 are located off of the gantry 34 and/or a joystick is used to move the gantry 34, the sensor 51 may communicate command signals to the gantry control module 85. The gantry control module 85 may then control respective actuators and/or motors to move the gantry in one or more directions associated with the six degrees of freedom of the gantry 34 as commanded.

Figure 2:
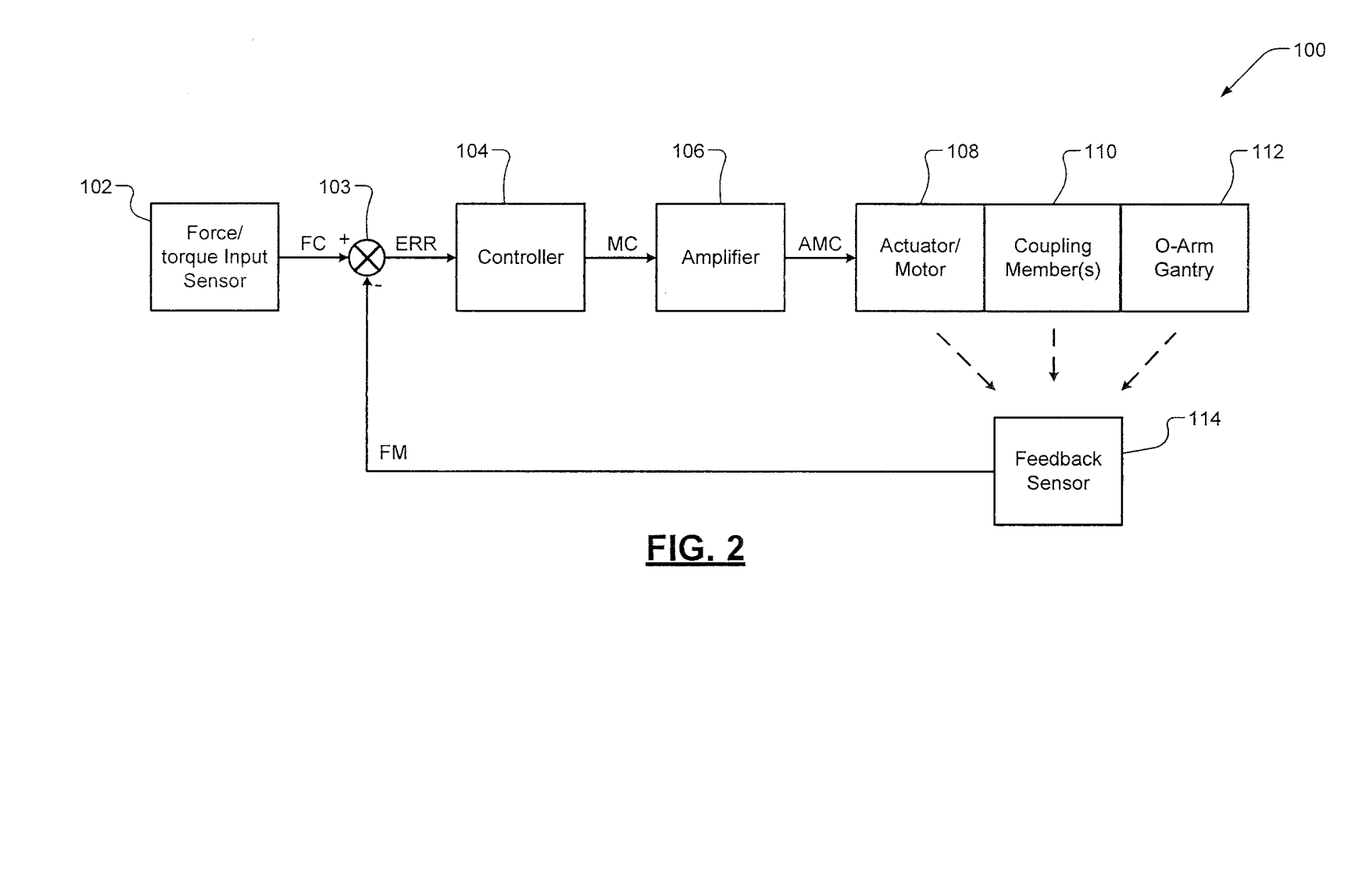
FIG. 2 is functional block diagram of a force-based example of a zero-force control system of the gantry positioning system of FIG. 1.

Zero-force control systems are described below with respect to FIGS. 2-5. Each of the zero-force control systems may be provided for one or more of the degrees of freedom of the gantry 34. In other words, although two zero-force control systems are shown in FIGS. 2 and 4, six zero-force control systems may be included in the gantry 34 and/or in one of the systems 16, 22, 32. Although FIGS. 2-5 are primarily described with respect to zero-control systems that are active control systems, zero-force movement and post movement position maintaining of a gantry may be provided without active control. For example, counterbalancing and friction devices may be included in the mobile cart 30, the imaging system 16, the image computing system 32 and/or in or separate from the gantry 34 that allow for (i) minimal force to move the gantry 34, and (ii) the gantry 34 to be held in a selected position. The counterbalancing devices and friction devices may be used for each degree of freedom. The counterbalancing devices may include, for example, weights and/or springs, which may be used to offset effects of gravity. The counterbalancing devices may be used to overcome friction, especially if the gantry 34 is not mobile in which case higher friction forces can be more prevalent. The friction devices may include, for example, brakes, pads having frictional materials, stopping elements, etc. Upon positioning the gantry 34, the friction devices may hold the gantry 34 in place, but yet allow for a minor amount of force and/or torque to overcome the corresponding friction and such that the gantry 34 can be easily repositioned.

Referring now also to FIG. 2, which shows a force-based example of at least a portion (or zero-force control system) 100 of the gantry positioning system 35. In the example shown, the zero-force control system 100 includes: a force/torque input sensor 102; a summer 103; a controller 104 (or force/torque module); an amplifier 106; an actuator (or servo motor) 108; one or more coupling members 110; an O-Arm gantry (e.g., the gantry 34 or other gantry) 112; and a feedback sensor 114.

The force/torque input sensor 102 may be, for example, the input sensor 51 and/or may include load cells, strain gauges and/or other force/torque sensors. The force/torque input sensor 102 may be a single sensor, load sensor, or strain gauge within the sensor 51. The actuator 108 may include and/or be implemented as a motor. The actuator 108 may be, for example, a series elastic actuator (SEA). As an example, a SEA may include a ballscrew driven by a motor. The SEA may further include a spring mounted axially at an end of the ballscrew (referred to as a series spring) to provide force control. The SEA may be a linear device or a rotary device. A SEA provides absorption of dynamic loading and is configured to prevent damage to the ballscrew. Deflection of the spring on the ballscrew may be sensed and used as a force feedback sensor (e.g., the force feedback sensor 114).

The coupling members 110 may include ballscrews, axels, belts, chains, gears, pulleys, brackets, springs, counterbalance devices, friction devices, etc. The coupling members 110 connect the actuator 108 to the O-arm gantry 112. The feedback sensor 114 may be similar to the force/torque input sensor 102 and include load cells, strain gauges and/or other force/torque sensors. The feedback sensor 114 may be located on the actuator 108, one of the coupling members 110, and/or the O-Arm gantry 112.

Figure 3:
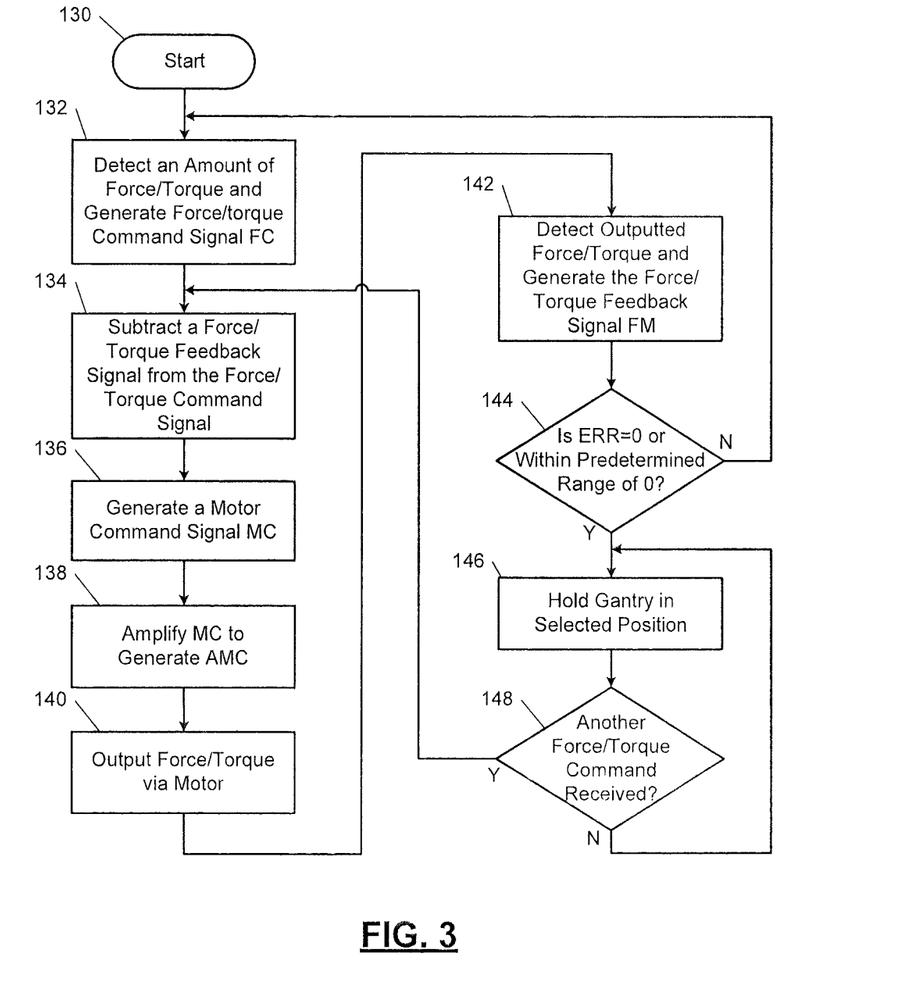
FIG. 3 illustrates a method of positioning a gantry and operating the zero-force control system of FIG. 2 in accordance with an embodiment of the present disclosure
Figure 4:
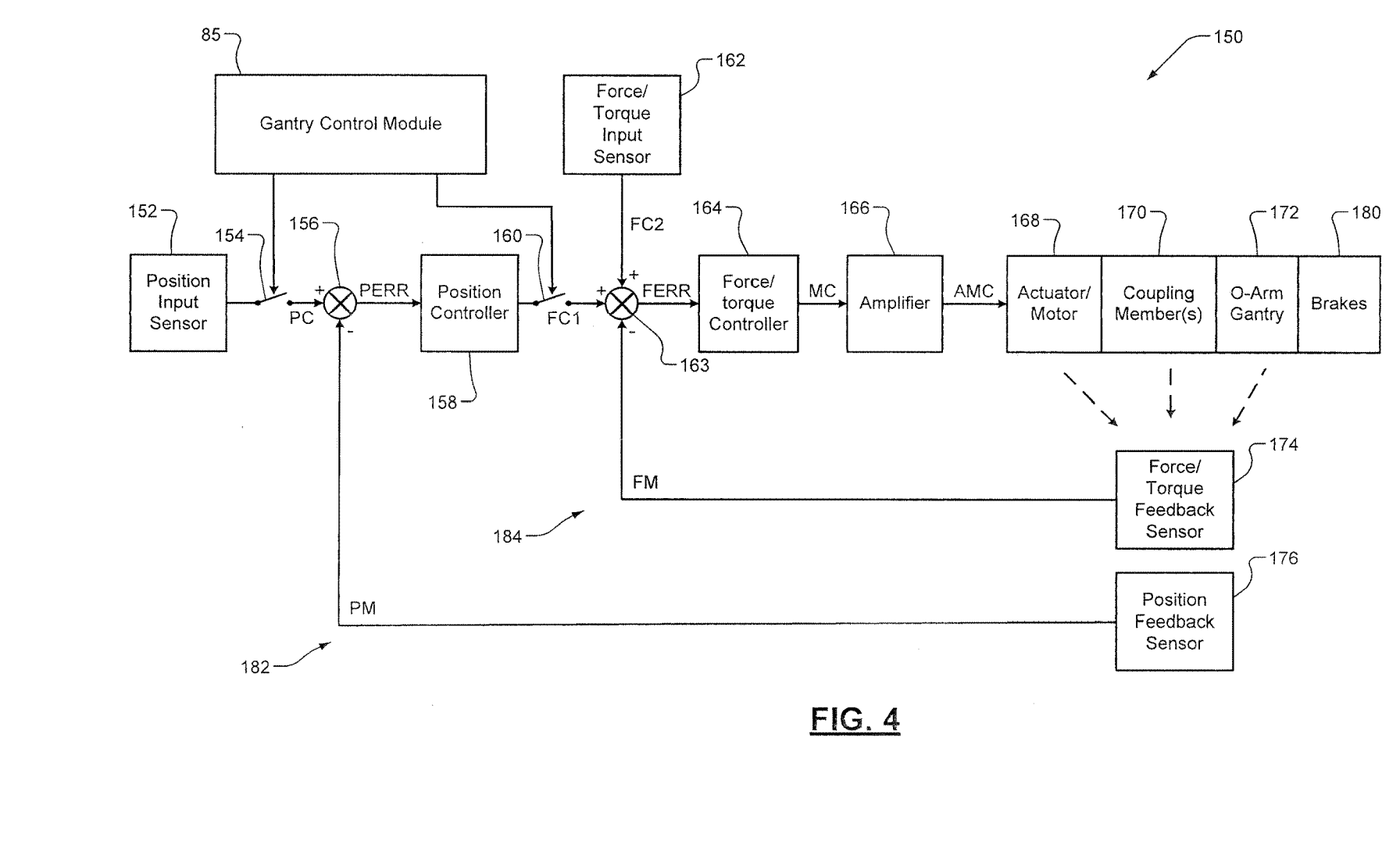
FIG. 4 is functional block diagram of a position and force-based example of a zero-force control system of the gantry positioning system of FIG. 1.

The zero-force control system 100 is further described with respect to the method of FIG. 3. FIG. 3 shows a method of positioning a gantry and operating the zero-force control system 100. Although the following tasks are primarily described with respect to the implementations of FIGS. 1-2, the tasks may be easily modified to apply to other implementations of the present disclosure. The tasks may be iteratively performed. The tasks may be implemented for each degree of freedom of the O-Arm gantry 112.

The method may begin at 130. At 132, the force/torque input sensor 102 detects an input force and/or torque applied to the handle 53 of FIG. 1, a handle of a joystick, or other movement device. The force and/or torque may be associated with movement of the O-Arm gantry 112 in a single direction corresponding to a single degree of freedom. The force/torque input sensor 102 generates a command signal FC, which may indicate an amount of force and/or an amount of torque.

At 134, the summer 103 subtracts a measured (or detected) feedback signal FM from the command signal FC. The feedback signal FM may be from the feedback sensor 114. The summer outputs an error signal ERR. At 136, the controller 104 receives the error signal ERR and generates a motor command signal MC. The controller 104 may be a proportional integral derivative (PID) controller or other suitable controller. The controller 104 may generate the motor command signal MC based on a zero reference force and/or torque (or other predetermined amount of force/torque). The controller 104 may control the actuator 108 to compensate for the error indicated by the error signal ERR and provide a net zero force and/or torque (or other predetermined amount of force/torque) at the handle 53 or other component of the O-Arm gantry 112. This provides counterbalancing.

At 138, the amplifier 106 amplifies the motor command signal MC to generate an amplified motor command signal AMC. At 140, the motor 108 outputs an amount of force/torque based on the amplified motor command signal AMC to move the O-Arm gantry 112 in a particular direction. The force/torque may be provided in a direction of the input force/torque detected by the force/torque input sensor 102 to provide the net force/torque at the handle 53 of zero (or other predetermined amount) or a net force/torque within a predetermined range of zero (or the other predetermined amount).

At 142, the feedback sensor 114 detects the outputted force/torque and generates the measured feedback signal FM, which is provided to the summer 103. Although not shown in FIG. 2, the output of the feedback sensor 114 may be signal processed to provide a force/torque signal comparable to the force/torque command signal FC. For example, the output of the feedback sensor 114 may be provided to the gantry control module 85, which may then convert the output of the feedback sensor 114 to provide the force/torque feedback signal FM that is comparable to the force/torque command signal FC.

At 144, if the error signal ERR is equal to zero (or other predetermined amount) or is within a predetermined range of zero (or the other predetermined amount), then task 146 is performed, otherwise task 132 may be performed. At 146, the O-Arm gantry 112 is held in the selected position. This may be done using brakes, friction devices, and/or other position maintaining devices. Some friction devices are disclosed above. Operation of brakes is further described with respect to FIGS. 4-5 below. At 148, if another force/torque command signal is received via the force/torque input sensor 102, task 134 may be performed, otherwise task 146 may be performed as shown or the method may end.

FIG. 2 provides a single force/torque based loop example. FIG. 4 provides a dual (or cascaded) loop example that is both position and force/torque based. Zero-force control for each of the degrees of freedom of the gantries disclosed herein may be implemented using various techniques. A couple of the techniques are described with respect to FIGS. 2-5. Although the zero-force control system of FIG. 4 is primarily described as having a force/torque control loop within a position control loop, the zero-force control system may include a velocity or acceleration control loop. The velocity or acceleration control loop may be included in addition to or as an alternative to the position control loop.

Referring now to FIG. 1 and FIG. 4, which shows a position and force-based example of at least a portion (or zero-force control system) 150 of the gantry positioning system 35 of FIG. 1. In the example shown, the zero-force control system 150 includes: the gantry control module 85; a position input sensor 152; a first switch 154, a first summer 156; a position controller (or position module) 158; a second switch 160; a force/torque input sensor 162; a second summer 163; a second (or force/torque) controller 164 (or force/torque module); an amplifier 166; an actuator (or servo motor) 168; one or more coupling members 170; an O-Arm gantry (e.g., the gantry 34 or other gantry) 172; a force/torque feedback sensor 174; and a position feedback sensor 176. The zero-force control system 150 may also include brakes 180 and/or friction devices. The first summer 156, the position controller 158, the second switch 160, the second summer 163, the force controller 164, the amplifier 166, the motor 168, the coupling members 170, the O-Arm gantry 172, and the position feedback sensor 176 are part of a position control loop 182 (referred to as the outer loop). The second summer 163, the force controller 164, the amplifier 166, the motor 168, the coupling members 170, the O-Arm gantry 172, and the force/torque feedback sensor 174 are part of a force/torque control loop 184 (referred to as the inner loop).

The position input sensor 152 may be, for example, the input sensor 51, a joystick, an encoder, an optical sensor, and/or other position sensor. The position input sensor 152 may be a single position, velocity and/or acceleration sensor within the sensor 51 and/or within a joystick. The force/torque input sensor 162 may be, for example, the input sensor 51 and/or may include load cells, strain gauges and/or other force/torque sensors. The force/torque input sensor 162 may be a single sensor, load sensor, or strain gauge within the sensor 51. The actuator 168 may include and/or be implemented as a motor. The actuator 168 may be, for example, a SEA. Deflection of a spring on a ballscrew of the SEA may be sensed and used as a force feedback sensor (e.g., the force/torque feedback sensor 174).

The coupling members 170 may include ballscrews, axels, belts, chains, gears, pulleys, brackets, springs, counterbalance devices, friction devices, etc. The coupling members 170 connect the actuator 168 to the O-arm gantry 172. The force/torque feedback sensor 174 may be similar to the force/torque input sensor 162 and include one or more load cells, strain gauges and/or other force/torque sensors. The force/torque feedback sensor 174 may be located on the actuator 168, one of the coupling members 170, and/or the O-Arm gantry 172. The position feedback sensor 176 may be similar to the position input sensor 152 and may include one or more encoders, optical sensors, and/or other position sensors.

Figure 5:
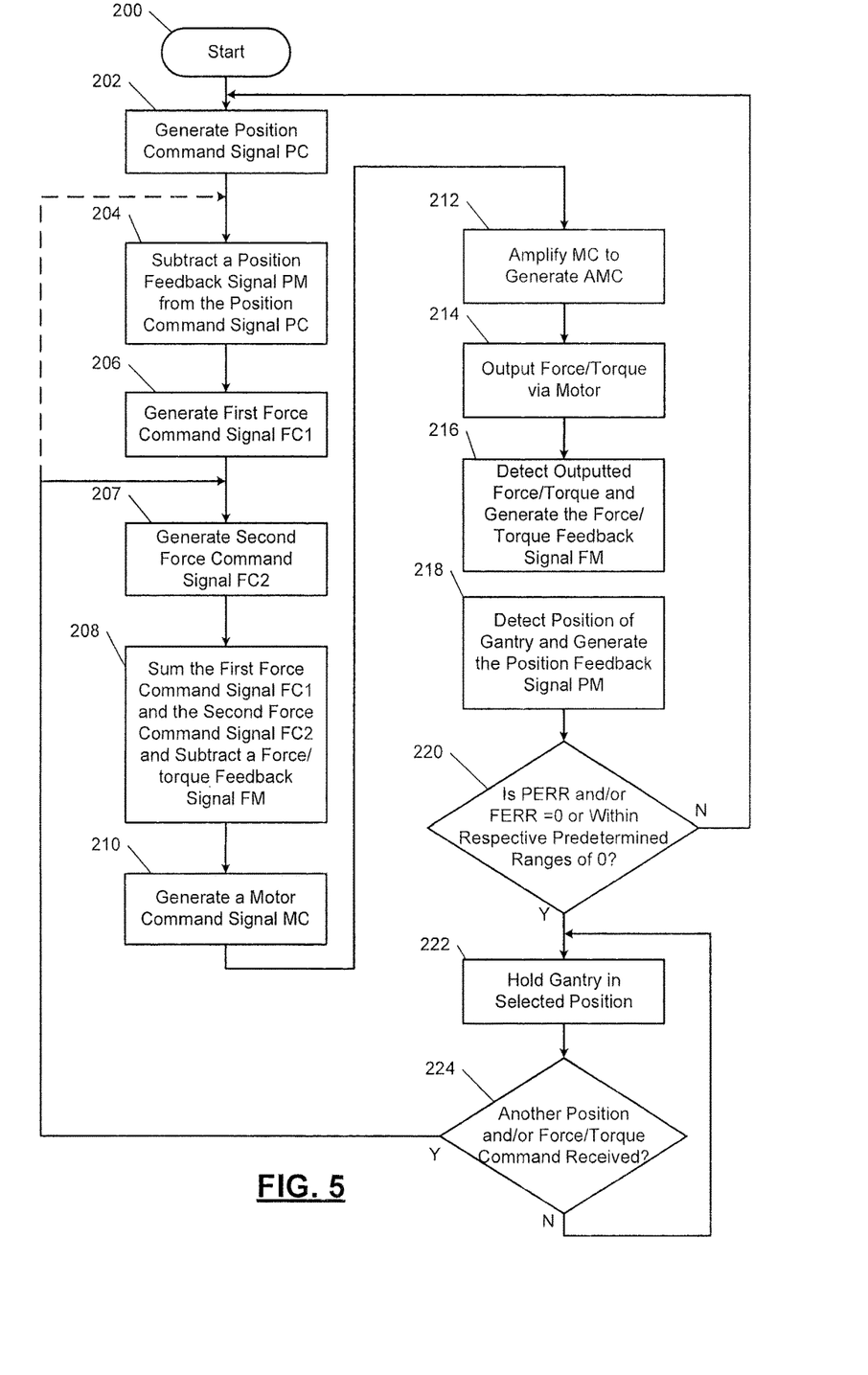
FIG. 5 illustrates a method of positioning a gantry and operating the zero-force control system of FIG. 4 in accordance with an embodiment of the present disclosure.

The zero-force control system 150 is further described with respect to the method of FIG. 5. FIG. 5 shows a method of positioning a gantry and operating the zero-force control system 150. Although the following tasks are primarily described with respect to the implementations of FIGS. 1 and 4, the tasks may be easily modified to apply to other implementations of the present disclosure. The tasks may be iteratively performed. The tasks may be implemented for each degree of freedom of the O-Arm gantry 172.

The method may begin at 200. The switches 154, 160 may be closed at 200 or may be in a closed state at 200 depending upon the operating mode. The first switch 154 controls whether position control is performed based on a position command signal. The second switch controls whether position control is provided via the position control loop 182.

At 202, the position input sensor 152 generates a position command signal PC. The position indicated by the position command signal PC may be associated with movement of the O-Arm gantry 112 in a single direction corresponding to a single degree of freedom. At 204, the first summer 156 sums the position command signal PC and a measured position feedback signal PM to generate a position error signal PERR. At 206, the position controller 158 receives the position error signal and generates a first force command signal FC1, which may indicate an amount of force or an amount of torque. The position controller 158 may be a PID controller or other suitable controller. The first force command signal FC1 may be based on the position error signal PERR and, for example, a table relating position errors to force/torque command values.

At 207, the force/torque input sensor 162 may generate a second force/torque command signal FC2, which may indicate a second amount of force and/or a second amount of torque. The force and/or torque may be associated with movement of the O-Arm gantry 172 in a single direction corresponding to a single degree of freedom.

At 208, the second summer 163 sums the first force/torque command signal FC1 and the second force/torque command signal FC2 from the force/torque input sensor 162. A force/torque feedback signal FM is subtracted from the sum of FC1 and FC2. The result of the subtraction is provided as a force/torque error signal FERR.

At 210, the force/torque controller 164 receives the force/torque error signal FERR and generates a motor command signal MC. The force/torque controller 164 may be a PID controller or other suitable controller. The force/torque controller 164 may generate the motor command signal MC based on a zero reference force and/or torque (or other predetermined amount of force/torque). The force/torque controller 164 may control the actuator 168 to compensate for the error indicated by the force/torque error signal FERR and provide a net zero force and/or torque (or the other predetermined amount of force/torque) at the handle 53 or other component of the O-Arm gantry 172. This provides counterbalancing.

At 212, the amplifier 166 amplifies the motor command signal MC to generate an amplified motor command signal AMC. At 214, the motor 168 outputs an amount of force/torque based on the amplified motor command signal AMC to move the O-Arm gantry 172 in a particular direction. The force/torque may be provided in a direction of the input force/torque detected by the force/torque input sensor 162 and/or in a direction indicated by the position input sensor 152. This provides a net force/torque at the handle 53 of zero (or the other predetermined amount of force/torque) or a net force/torque within a predetermined range of zero (or the other predetermined amount of force/torque).

At 216, the force/torque feedback sensor 174 detects the outputted force/torque and generates the measured force/torque feedback signal FM, which is provided to the second summer 163. Although not shown in FIG. 4, the output of the force/torque feedback sensor 174 may be signal processed to provide a force/torque signal comparable to the force/torque command signals FC1, FC2. For example, the output of the force/torque feedback sensor 174 may be provided to the gantry control module 85, which may then convert the output of the force/torque feedback sensor 174 to provide the force/torque feedback signal FM that is comparable to the force/torque command signals FC1, FC2.

At 218, the position feedback sensor 176 may generate the position feedback signal PM, which is provided to the first summer 156. The position feedback signal PM may be indicative of a position of the O-Arm gantry 172 for the corresponding degree of freedom of motion. Although not shown in FIG. 4, the output of the position feedback sensor 176 may be signal processed to provide a position signal comparable to the position command signal PC. For example, the output of the position feedback sensor 176 may be provided to the gantry control module 85, which may then convert the output of the position feedback sensor 176 to provide the position feedback signal PM that is comparable to the position command signal PC.

At 220, if the position error signal PERR and/or the force/torque error signal FERR are equal to zero and/or are within predetermined respective ranges of zero, then task 222 may be performed, otherwise task 202 or 207 may be performed.

At 222, the O-Arm gantry 172 is held in the selected position. This may be done using the brakes 180, friction devices, and/or other position maintaining devices. Some friction devices are disclosed above. The gantry control module may monitor command signals PC, FC1, FC2, the error signals PERR, FERR and/or the feedback signals FM, PM and control the brakes 180 based on these signals. At 224, if another position command signal and/or force/torque command signal is received via the input sensors 152, 162, task 204 and/or 207 may be performed, otherwise task 222 may be performed as shown or the method may end.

Alternatively, the gantry control module 85 may open switch 154 such that the selected position is maintained via the position control loop PM where the position command signal PC is zero since the switch is open. When the position command signal is zero, this indicates to the position control loop to maintain the current position. When the first switch 154 is in an OPEN state, the position control loop may not receive an input from the position input sensor 152. The first switch 154 may be opened to maintain a current position, for example, a position previously selected via the position input sensor 152 and/or the force/torque input sensor 162. As a result, the position control loop 182 is converted from controlling movement of the O-Arm gantry 172 (or operating in a movement control mode) to maintaining position of the O-Arm gantry 172 (or operating in a position maintaining mode).

If the first switch 154 is open, the O-Arm gantry 172 may be manipulated into a selected position via the force/torque input sensor 162. Once the O-Arm gantry 172 is in a selected position, an output of the force/torque input sensor 162 may return to zero. The position control loop 182 may then hold the O-Arm gantry 172 in the selected position.

The above-described tasks of FIGS. 3 and 5 are meant to be illustrative examples; the tasks may be performed sequentially, synchronously, simultaneously, continuously, during overlapping time periods or in a different order depending upon the application. Also, any of the tasks may not be performed or skipped depending on the implementation and/or sequence of events.

Cascaded control loop combinations other than the control loop combination of FIG. 4 may be implemented. Inner loops and outer loops of the control loop combinations may detect position, velocity, and force/torque based on the configurations of the control loops. Table 1 below provides examples of cascaded inner and outer loop combinations and respective parameters detected and controlled by each of the loops.

|  |  | Inner Loop | | |
| --- | --- | --- | --- | --- |
|  |  | Position | Velocity | Force/Torque |
| Outer Loop | Position |  | X | X |
|  | Velocity | X |  | X |
|  | Force/Torque | X | X |  |

The above-described examples provide rapid positioning of a gantry 34 with minimal effort by a user. Quick positioning of a gantry reduces surgery preparation time. The gantry can be moved with minimally applied user force due to the counterbalancing provided by the zero-force control systems for each degree of freedom of motion of the gantry. The gantry can be moved without the need of a second person, as the user can easily move the gantry and see areas of interest due to the placement of a corresponding component (e.g., the handle 53 of FIG. 1), a joystick and/or other input control device.

The wireless communications described in the present disclosure can be conducted in full or partial compliance with IEEE standard 802.11-2012, IEEE standard 802.16-2009, IEEE standard 802.20-2008, and/or Bluetooth Core Specification v4.0. In various implementations, Bluetooth Core Specification v4.0 may be modified by one or more of Bluetooth Core Specification Addendums 2, 3, or 4. In various implementations, IEEE 802.11-2012 may be supplemented by draft IEEE standard 802.11ac, draft IEEE standard 802.11ad, and/or draft IEEE standard 802.11ah.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A OR B OR C), using a non-exclusive logical OR, and should not be construed to mean "at least one of A, at least one of B, and at least one of C." It should be understood that one or more steps within a method may be executed in different order (or concurrently) without altering the principles of the present disclosure.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. A system comprising:
    a first input sensor configured to (i) detect a first amount of force or torque applied by a user of an x-ray scanner gantry in a first direction, and (ii) generate a first input command signal, wherein the first input command signal indicates the first amount of force or torque;
    a first controller configured to control operation of a motor based at least on a first feedback signal to provide counterbalancing of the x-ray scanner gantry in the first direction; and
    a first feedback sensor configured to (i) detect a second amount of force or torque applied on the x-ray scanner gantry in the first direction as a result of the controlled operation of the motor, and (ii) generate the first feedback signal based on the detected second amount of force or torque.

2. The system of claim 1, wherein the first controller is configured to control operation of the motor based at least on the first feedback signal to further provide a net force or torque on the x-ray scanner gantry in the first direction that is equal to a predetermined value or is within a predetermined range of the predetermined value.

3. The system of claim 1, wherein:
the first controller is configured to generate a motor command signal based on a first error signal; and
the motor is configured to apply the second amount of force or torque on the x-ray scanner gantry in the first direction based on the motor command signal.

4. The system of claim 3, further comprising a first summer configured to generate the first error signal based on the first input command signal and the first feedback signal.

5. The system of claim 1, further comprising a handle mounted on the first input sensor, wherein the first input sensor comprises a load cell or a strain gauge.

6. The system of claim 4, further comprising a second controller configured to generate an output signal,
wherein the first summer is configured to generate the first error signal based on the output signal.

7. The system of claim 6, further comprising:
a second input sensor configured to (i) detect movement of a first component, and (ii) generate a second input command signal, wherein the second input command signal commands movement of the x-ray scanner gantry in the direction;
a second summer configured to generate a second error signal based on the second input command signal and a second feedback signal,
wherein the second controller is configured to generate the output signal based on the second error signal; and
a second feedback sensor configured to generate the second feedback signal based on the result of the controlled operation of the motor.

8. The system of claim 7, further comprising:
a switch configured to connect the second input sensor to the second summer to move the x-ray scanner gantry to a user selected position; and
a control module configured to change a state of the switch to maintain the user selected positon of the x-ray scanner gantry as a result of the first amount of force or torque applied by the user on the first component.

9. The system of claim 7, further comprising:
a switch configured to disconnect a position control loop of the system, wherein the position control loop includes the second summer, the second controller and the second feedback sensor; and
a control module configured to change a state of the switch to transition between a first mode and a second mode, wherein
during the first mode, the position control loop is connected and the first controller is providing the net force or torque based on both the first input command signal and the second input command signal, and
during the second mode, the position control loop is disconnected and the first controller is providing the net force or torque based on the first input command signal and not the second input command signal.

10. A system comprising:
an input sensor configured to (i) detect movement of a first component of an x-ray scanner gantry by a user, and (ii) generate an input command signal, wherein the input command signal commands movement of the x-ray scanner gantry in a direction;
a controller configured to control operation of a motor based at least on a feedback signal to provide a net force on the x-ray scanner gantry in the direction that is equal to a predetermined value or is within a predetermined range of the predetermined value; and
a feedback sensor configured to (i) detect movement of the x-ray scanner gantry in the direction as a result of the controlled operation of the motor, and (ii) generate the feedback signal based on the detected movement.

11. The system of claim 10, wherein the predetermined value is zero.

12. The system of claim 10, wherein the first component is a handle mounted on the input sensor, and the input sensor is a load cell or strain guage.

13. The system of claim 10, wherein the movement of the first component is detected based on a change in position of the first component, a change in velocity of the first component, or a change in acceleration of the first component.

14. The system of claim 10, wherein:
the input command signal indicates a position of the first component; and
the feedback signal indicates a position of a second component of the x-ray scanner.

15. The system of claim 10, wherein the controller is configured to control operation of the motor based at least on the feedback signal to further provide counterbalancing of the x-ray scanner gantry in the direction.

16. The system of claim 10, further comprising a summer configured to generate an error signal based on the input command signal and the feedback signal, wherein the controller is configured to generate a motor command signal based on the error signal.

17. The system of claim 16, wherein the motor is configured to move the x-ray scanner gantry in the direction based on the motor command signal.

18. A method comprising:
detecting, via a first input sensor, a first amount of force or torque applied by a user on a component of an x-ray scanner gantry in a first direction;
generating a first input command signal, wherein the first input command signal indicates the first amount of force or torque;
controlling operation of a motor based at least on a first feedback signal to provide counterbalancing of the x-ray scanner gantry in the first direction;
detecting, via a first feedback sensor, a second amount of force or torque applied on the x-ray scanner gantry in the first direction as a result of the controlled operation of the motor; and
generating the first feedback signal based on the second amount of force or torque.

19. The method of claim 18, further comprising:
generating a first error signal based on the first input command signal and the first feedback signal; and
controlling operation of the motor based on the first error signal.

20. The method of claim 19, further comprising:
detecting, via a second input sensor, movement of the component;
generating a second input command signal, wherein the second input command signal commands movement of the x-ray scanner gantry in the direction;
generating a second error signal based on the second input command signal and a second feedback signal, wherein an output signal is generated based on the second error signal; and generating, via a second feedback sensor, the second feedback signal based on the result of the controlled operation of the motor.

* * * * *